(12) United States Patent
Berwe et al.

(10) Patent No.: US 7,351,823 B2
(45) Date of Patent: Apr. 1, 2008

(54) PREPARATION PROCESS

(75) Inventors: Mathias Berwe, Sprockhövel (DE);
Christian Thomas, Wuppertal (DE);
Joachim Rehse, Leichlingen (DE);
Dirk Grotjohann, Leverkusen (DE)

(73) Assignee: Bayer HealthCare AG, Leverkusen (DE)

( * ) Notice: Subject to any disclaimer, the term of this patent is extended or adjusted under 35 U.S.C. 154(b) by 535 days.

(21) Appl. No.: 11/032,815

(22) Filed: Jan. 10, 2005

(65) Prior Publication Data

US 2005/0182055 A1    Aug. 18, 2005

(30) Foreign Application Priority Data

Jan. 15, 2004   (DE) .................... 10 2004 002 044

(51) Int. Cl.
*C07D 413/10* (2006.01)

(52) U.S. Cl. .................................... 544/137

(58) Field of Classification Search ............... None
See application file for complete search history.

(56) References Cited

FOREIGN PATENT DOCUMENTS

| WO | 0147919 | 7/2001 |
|---|---|---|
| WO | 2004060887 | 7/2004 |

OTHER PUBLICATIONS http://familydoctor.org/online/famdocen/home/common/heart-disease/basics/290.html.*

* cited by examiner

*Primary Examiner*—Rebecca Anderson
*Assistant Examiner*—Sun Jae Y Loewe

(57) ABSTRACT

The present invention relates to a process for preparing 5-chloro-N-({(5S)-2-oxo-3-[4-(3-oxo-4-morpholinyl)phenyl]-1,3-oxazolidin-5-yl}methyl)-2-thiophenecarboxamide starting from 2-[(2S)-2-oxiranylmethyl]-1H-isoindole-1,3(2H)-dione, 4-(4-aminophenyl)-3-morpholinone and 5-chlorothiophene-2-carbonyl chloride.

14 Claims, No Drawings

PREPARATION PROCESS

The present invention relates to a process for preparing 5-chloro-N-({(5S)-2-oxo-3-[4-(3-oxo-4-morpholinyl)phenyl]-1,3-oxazolidin-5-yl}methyl)-2-thiophenecarboxamide starting from 2-[(2S)-2-oxiranylmethyl]-1H-isoindole-1,3 (2H)-dione, 4-(4-aminophenyl)-3-morpholinone and 5-chlorothiophene-2-carbonyl chloride.

The compound 5-chloro-N-({(5S)-2-oxo-3-[4-(3-oxo-4-morpholinyl)phenyl]-1,3-oxazolidin-5-yl}-methyl)-2-thiophenecarboxamide is disclosed in WO-A 01/47919 and corresponds to the formula (I)

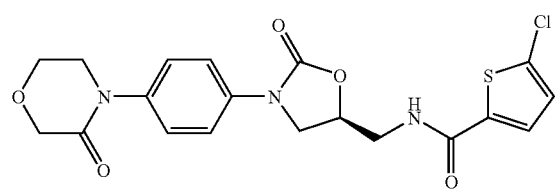

(I)

The compound of the formula (I) acts as inhibitor of clotting factor Xa and can be employed as agent for the prophylaxis and/or treatment of thromboembolic disorders, in particular myocardial infarction, angina pectoris (including unstable angina), reocclusions and restenoses after angioplasty or aortocoronary bypass, stroke, transient ischaemic attacks, peripheral arterial occlusive diseases, pulmonary embolisms or deep venous thromboses.

WO-A 01/47919 also describes a method for preparing the compound of the formula (I) in the gram range starting from the same starting compounds 2-[(2S)-2-oxiranylmethyl]-1H-isoindole-1,3(2H)-dione (II), 4-(4-aminophenyl)-3-morpholinone (III) and 5-chlorothiophene-2-carbonyl chloride (IV):

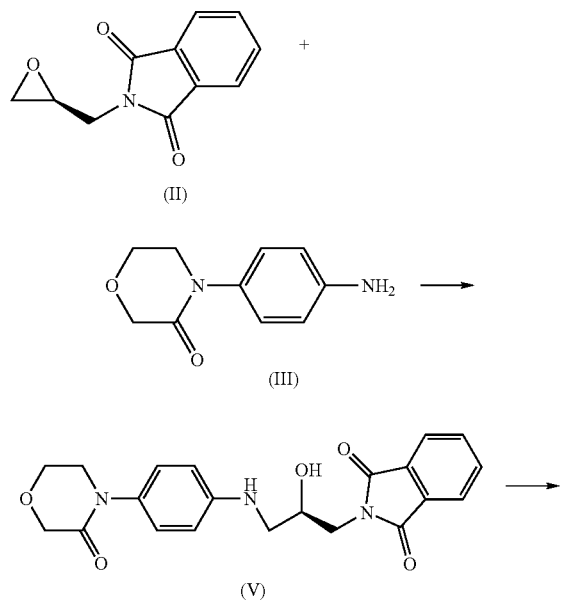

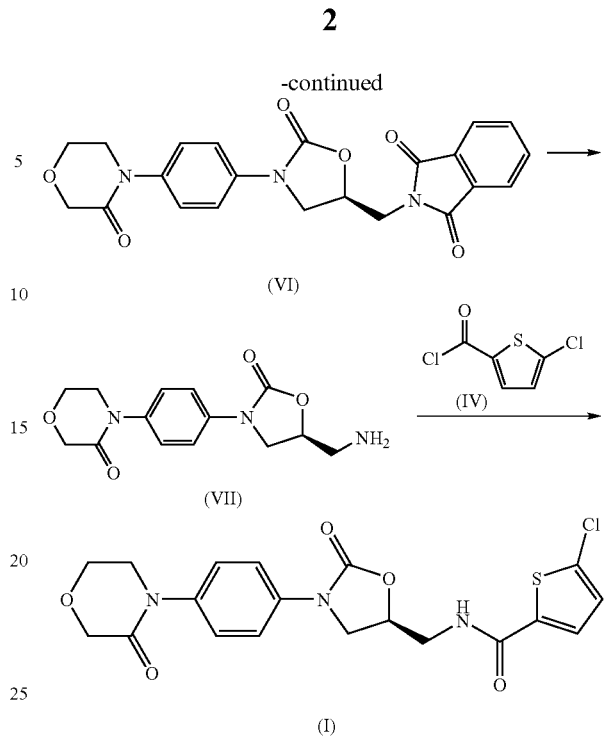

In this case, 2-[(2S)-2-oxiranylmethyl]-1H-isoindole-1,3 (2H)dione (II) is reacted with 4-(4-aminophenyl)-3-morpholinone (III) to give 2-((2R)-2-hydroxy-3-{[4-(3-oxo-4-morpholinyl)-phenyl]amino}propyl)-1H-isoindole-1,3(2H) dione (V). Subsequently, (V) is converted with a phosgene equivalent into 2-({(5S)-2-oxo-3-[4-(3-oxo-4-morpholinyl) phenyl]-1,3-oxazolidin-5-yl}-methyl)-1H-isoindole-1,3 (2H)dione (VI). Elimination of the phthalimide protective group affords 4-{4-[(5S)-5-(aminomethyl)-2-oxo-1,3-oxazolidin-3-yl]phenyl}morpholine-3-one (VII) which is finally reacted with 5-chlorothiophene-2-carbonyl chloride (IV) to give 5-chloro-N-({(5S)-2-oxo-3-[4-(3-oxo-4-morpholinyl)phenyl]-1,3-oxazolidin-5-yl}methyl)-2-thiophenecarboxamide (I).

However, this process disclosed in WO-A 01/47919 exhibits various disadvantages in the reaction management which has particularly unfavourable effects for preparation of the compound of the formula (I) on the industrial scale.

DE 10300111.5 discloses an alternative process for synthesizing the compound of the formula (I) starting from 5-chlorothiophene-2-carbonyl chloride (IV), (2S)-3-aminopropane-1,2-diol hydro-chloride (VIII) and 4-(4-aminophenyl)-3-morpholinone (III):

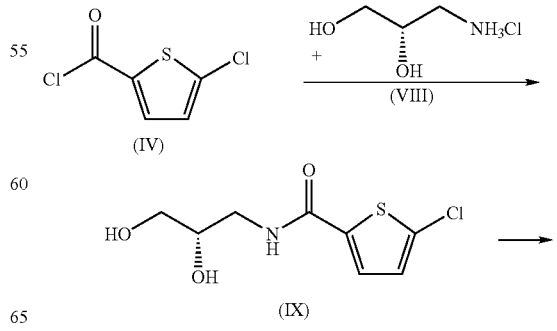

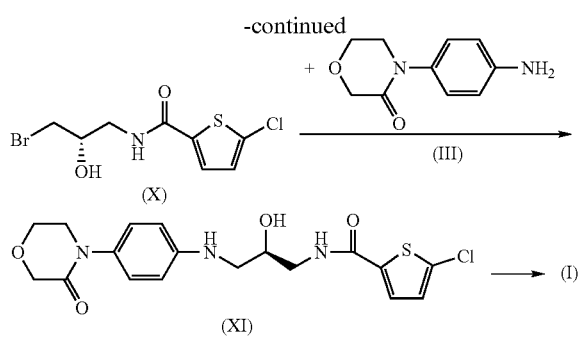

In this case, 5-chlorothiophene-2-carbonyl chloride (IV) is reacted with (2S)-3-aminopropane-1,2-diol hydrochloride (VII) to give 5-chlorothiophene-2-carboxylic acid ((S)-2,3-dihydroxypropyl)-amide (IX). Subsequently, (IX) is converted into 5-chlorothiophene-2-carboxylic acid ((S)-3-bromo-2-hydroxypropyl)amide (X), which is then reacted with 4-(4-aminophenyl)-3-morpholinone (III) to give 5-chlorothiophene-2-carboxylic acid {(R)-2-hydroxy-3-[4-(3-oxomorpholin-4-yl)phenylamino]-propyl}amide (XI). Finally, (XI) is reacted with phosgene or a phosgene equivalent to give 5-chloro-N-({(5S)-2-oxo-3-[4-(3-oxo-4-morpholinyl)phenyl]-1,3-oxazolidin-5-yl}methyl)-2-thiophenecarboxamide (I).

This alternative synthesis can be carried out on an industrial scale, although toxic solvents or reagents are used in part. This is disadvantageous per se, and in addition these toxic substances must be removed from the final product (I) until below the maximum limit permissible in each case in the product for regulatory reasons, which signifies additional expense.

The object of the present invention derives therefrom, of providing a simplified process for preparing the compound (I) on the industrial scale, avoiding toxic solvents or reagents, especially in the last steps of the process.

It has now been found, surprisingly, that it is possible by modifying certain reaction parameters in the synthesis disclosed in WO-A 01/47919 to prepare the compound of the formula (I) optionally in larger amounts in good yield and purity.

The present invention thus relates to a process for preparing 5-chloro-N-({(5S)-2-oxo-3-[4-(3-oxo-4-morpholinyl)phenyl]-1,3-oxazolidin-5-yl}methyl)-2-thiophenecarboxamide of the formula (I) by reacting 4-{4-[(5S)-5-(aminomethyl)-2-oxo-1,3-oxazolidin-3-yl]phenyl}morpholin-3-one (VII) hydrochloride with 5-chlorothiophene-2-carbonyl chloride (IV), characterized in that the reaction is carried out in a solvent selected from the group of ether, alcohol, ketone and water or in a mixture thereof with use of an inorganic base.

Examples of suitable and preferred solvents which may be mentioned are: ethers such as tetrahydrofuran, dioxane, diisopropyl ether or methyl tert-butyl ether; alcohols such as methanol, ethanol, isopropanol, n-propanol, n-butanol, isobutanol, sec-butanol or tert-butanol; ketones such as methyl ethyl ketone, methyl isobutyl ketone or acetone or water or mixtures of two or more of the solvents listed.

Particularly preferred solvents are ketones or mixtures of ketones with water, especially acetone or, preferably, mixtures of acetone with water.

Examples of suitable and preferred inorganic bases which may be mentioned are: alkali metal (e.g. sodium and potassium) and alkaline earth metal (e.g. calcium and magnesium) hydroxides, alkali metal and alkaline earth metal carbonates or alkali metal and alkaline earth metal bicarbonates.

Particularly preferred as inorganic base are sodium hydroxide, sodium carbonate or sodium bicarbonate, especially sodium carbonate.

The reaction of aminomethyloxazolidinone (VII) hydrochloride with chlorothiophenecarbonyl chloride (IV) is preferably carried out in an acetone/water mixture as solvent with use of sodium carbonate as base.

The acetone/water ratio can in this case be varied over a wide range, and is preferably from 0.5 to 1.5 (v/v), in particular 0.9 to 1.1 (v/v).

In this way it is possible firstly to avoid the carcinogenic pyridine which is used as solvent and base in the process described in WO-A 01/47919. It is additionally possible according to the invention to avoid the clinically complicated chromatographic purification of the product (I).

The process according to the invention is carried out by preferably initially charging an aqueous sodium carbonate solution, into which firstly acetone and then aminomethyloxazolidinone (VII) hydrochloride and subsequently, chlorothiophenecarbonyl chloride (IV) are introduced. The addition of the reactants preferably takes place at a temperature between 0 and 20° C., in particular between 10 and 15° C. After the addition has taken place, the reaction mixture is then stirred at a temperature between 40 and 55° C., preferably at about 50° C. After cooling to room temperature, the product can then be isolated in a simple manner by filtration.

In a preferred embodiment of the present invention, the crude product of the compound of the formula (I) which is obtained by the filtration described above is recrystallized for further purification from acetic acid in a subsequent step.

Aminomethyloxazolidinone (VII) is prepared, as already disclosed also in WO-A 01/47919, by eliminating the phthalimide protective group from oxazolidinonemethylphthalimide (VI) with methylamine in ethanol as solvent. However, after the reaction has taken place, unlike the description in WO-A 01/47919, aqueous hydrochloric acid is then added at elevated temperature to the reaction mixture until the pH is between 1 and 4, preferably between 2 and 3. The addition takes place at elevated temperature, preferably at a temperature between 50 and 60° C. In this way, aminomethyloxazolidinone (VII) is isolated pure in the form of its hydrochloride, which in this case results as crystals and easily filterable, in a simple manner.

The process disclosed in WO-A 01/47919, in which the aminomethyloxazolidinone (VII) crude product obtained after concentration of the reaction mixture is directly employed in the further reaction with chlorothiophenecarbonyl chloride (IV), has by contrast the disadvantage that the secondary components of this reaction, which are present in the aminomethyloxazolidinone (VII) crude product, impede the subsequent preparation of the final product (I) and additionally contaminate the product (I). In contrast thereto, the use of aminomethyloxazolidinone (VII) isolated according to the invention as solid hydrochloride in pure form makes improved reaction management possible in the following reaction with chlorothiophenecarbonyl chloride (IV), with unwanted side reactions being avoided and a purer product being obtained, so that the elaborate chromatographic purification can be avoided.

Oxazolidinonemethylphthalimide (VI) is prepared, as already disclosed also in WO-A 01/47919, by cyclization of the hydroxyamino compound (V) with a phosgene equivalent, for example and preferably with N,N-carbonyldiimidazole. However, the reaction conditions differ from those disclosed in WO-A 01/47919 in that the reaction is carried out not in the presence of dimethylaminopyridine as catalyst and tetrahydrofuran as solvent but according to the invention without catalyst in N-methylpyrrolidone or toluene, preferably in toluene as solvent. This also makes it possible to isolate the resulting oxazolidinonemethylphthalimide (VI) by simple filtration, instead of by elaborate chromatographic purification.

The hydroxyamine (V) is prepared, as already disclosed also in WO-A 01/47919, by reacting (S)-epoxyphthalimide (II) with anilinomorpholinone (III) in aqueous ethanol as solvent at a reaction temperature of 60° C. However, unlike the disclosure in WO-A 01/47919, the ethanol/water ratio (v/v) is according to the invention 1:1 to 1:3, preferably 1:2 (v/v), instead of 9:1, and subsequent metering in of the precursor (II) is no longer necessary. Instead, the reaction mixture is stirred at a temperature between 55 and 65° C. for between 24 and 48 hours, preferably about 36 hours.

In a preferred embodiment of the present invention, seed crystals of the reaction product (V) are added to the reaction mixture after the reaction has lasted one to two hours, so that the reaction product starts to crystallize out.

In a particularly preferred embodiment of the present invention, the reaction mixture is heated under reflux towards the end of the reaction time, with the suspension being retained, and is then cooled again to the reaction temperature between 55 and 65° C.

This heating to reflux is repeated where appropriate, the heating preferably taking place twice in total.

Synthesis of the (S)-epoxyphthalimide (II) starting compound is described for example in A. Gutcait et al. *Tetrahedron Asym*. 1996, 7, 1641. In addition, the substance is commercially available, for example from Daiso Ltd., Japan.

Synthesis of the anilinomorpholinone (III) starting compound is described in detail for example in WO-A 01/47919, page 55 to 57 or in DE 10342570.5.

The individual stages of the process according to the invention can be carried out under atmospheric, elevated or reduced pressure (e.g. from 0.5 to 5 bar). Unless indicated otherwise, atmospheric pressure is generally used.

The invention is explained in detail below by a preferred exemplary embodiment, but is not restricted thereto. Unless indicated otherwise, all quantitative data related to percentages by weight.

Synthesis of 5-chloro-N-({(5S)-2-oxo-3-[4-(3-oxo-4-morpholinyl)phenyl]-1,3-oxazolidin-5-yl}-methyl)-2-thiophenecarboxamide (I)

a) 2-((2R)-2-Hydroxy-3-{[4-(3-oxo-4-morpholinyl)phenyl]amino}propyl)-1H-isoindole-1,3(2H)-dione (V)

1173 g of 2-[(2S)-2-oxiranylmethyl]-1H-isoindole-1,3 (2H)dione (II) and 4-(4-aminophenyl)-3-morpholinone (III) are mixed at 20° C. with 6.7 l of water and 14.4 l of ethanol. The suspension is heated to 58 to 60° C., and the resulting solution is stirred for 36 hours. After 2 hours, 5 g of crystalline 2-((2R)-2-hydroxy-3-{[4-(3-oxo-4-morpholinyl)phenyl]amino}propyl)-1H-isoindole-1,3(2H)-dione (V) are added to the reaction mixture, after which the product starts to crystallize. After cooling to 26° C., the precipitated reaction product is filtered off with suction, washed with ethanol and then dried.

Yield: 1522 g; equivalent to 81.4% of theory. Melting point: 215° C.

b) 2-({(5S)-2-Oxo-3-[4-(3-oxo-4-morpholinyl)phenyl]-1,3-oxazolidin-5-yl}methyl)-1H-isoindole-1,3 (2H)-dione (VI)

2641 g of 2-((2R)-2-hydroxy-3-{[4-(3-oxo-4-morpholinyl)phenyl]amino}propyl)-1H-isoindole-1,3(2H)-dione (V) are suspended in 22 l of toluene and, at 19° C., 1300 g of N,N-carbonyl-diimidazole are added. The reaction mixture is subsequently heated under reflux for one hour and then, at 60° C., 4.5 l of ethanol are added. After cooling to 25 to 30° C., the precipitated reaction product is filtered off with suction, washed with ethanol and then dried.

Yield: 2756 g; equivalent to 97.9% of theory. Melting point: 220.5° C.

c) 4-{4-[(5S)-5-(Aminomethyl)-2-oxo-1,3-oxazolidin-3-yl]phenyl}morpholin-3-one (VII)

1360 g of 2-({(5S)-2-oxo-3-[4-(3-oxo-4-morpholinyl) phenyl]-1,3-oxazolidin-5-yl}methyl)-1H-isoindole-1,3 (2H)-dione (VI) are suspended in 10.2 l of ethanol at 22° C., and 1103 g of methylamine solution (40% strength in water) are added. The reaction mixture is then heated to 60 to 63° C., and the resulting solution is stirred at this temperature for 2 hours. After cooling to 55 to 60° C., a total of 2348 g of hydrochloric acid solution (20% strength in water) is added until the pH is 2.7, after which the product starts to crystallize. After cooling to 20° C., the precipitated reaction product is filtered off with suction, washed with methanol and then dried.

Yield: 875 g; equivalent to 82.7% of theory. Melting point: decomposition above 280° C. $^1$H NMR (300 MHz, $d_6$-DMSO): 3.25 (m, 2H), 3.72 (m, 2H), 3.98 (m, 3H), 4.42 (m, 3H), 4.97 (m, 1H), 7.42 (d, 2H, J=9.0 Hz), 7.57 (d, 2H, J=9.0 Hz), 8.44 (s (br.), 3H) ppm.

d) 5-Chloro-N-({(5S)-2-oxo-3-[4-(3-oxo-4-morpholinyl)phenyl]-1,3-oxazolidin-5-yl}-methyl)-2-thiophenecarboxamide (I)

1st Step: 5-chlorothiophene-2-carbonyl chloride (IV)

3.00 kg of 5-chlorothiophene-2-carboxylic acid (commercially available) are suspended in 8.48 kg of toluene and heated to 75 to 80° C. At this temperature, 2.63 kg of thionyl chloride are added dropwise over a period of 85 minutes, followed by stirring at 75 to 80° C. for 30 minutes and then at the reflux temperature until gas evolution ceases. After cooling, the reaction mixture is distilled under reduced pressure with gradually increasing internal temperature (up to a maximum of 60° C.) to remove excess thionyl chloride and toluene until an approximately 30% strength solution of the acid chloride in toluene is produced.

2nd Step: 5-Chloro-N-({(5S)-2-oxo-3-[4-(3-oxo-4-morpholinyl)phenyl]-1,3-oxazolidin-5-yl}-methyl)-2-thiophenecarboxamide (I)—Crude Product 1160 g of 4-{4-[(5S)-5-(aminomethyl)-2-oxo-1,3-oxazolidin-3-yl]phenyl}morpholin-3-one (VII) hydrochloride, 350 ml of water and 2.7 l of acetone are successively added to a solution of 464 g of sodium carbonate in 5.95 l of water at 10° C. At 8 to 12° C., 2535 g of 5-chlorothiophene-2-carbonyl chloride (IV) (30% strength solution in toluene) and a further 517 ml of toluene are added. The reaction mixture is then heated to 50° C., 2700 ml of acetone are added, and the mixture is stirred at 50 to 53° C. for a further 30 minutes. After cooling to 26° C., the precipitated reaction product is filtered off with suction and washed with water and acetone.

Yield: 1998 g of solvent-containing crude product.

The residual moisture content is found to be 24.3%, which corresponds to a calculated dry weight of 1505 g or 98.7% of theory.

3rd Step: 5-Chloro-N-({(5S)-2-oxo-3-[4-(3-oxo-4-morpholinyl)phenyl]-1,3-oxazolidin-5-yl}-methyl)-2-thiophenecarboxamide (I)—Recrystallization 2120 g of solvent-containing crude product (residual moisture content 9.4%) is suspended in 12 kg of acetic acid and heated to 110 to 115° C. The resulting solution is stirred at this temperature for 10 minutes and then, after clarifying filtration, cooled to 20° C. The precipitated product is filtered off with suction, washed with acetic acid and water and then dried.

Yield: 1818 g; equivalent to 94.7% of theory (based on the dry weight of the crude product). Melting point: 230° C.

The invention claimed is:

1. Process for preparing 5-chloro-N-({(5S)-2-oxo-3-[4-(3-oxo-4-morpholinyl)phenyl]-1,3-oxazolidin-5-yl}methyl)-2-thiophenecarboxamide, comprising reacting 4-{4-[(5S)-5-(aminomethyl)-2-oxo-1,3-oxazolidin-3-yl]phenyl}morpholin-3-one hydrochloride with 5-chlorothiophene-2-carbonyl chloride, wherein the reaction is carried out in a solvent selected from the group of ether, alcohol, ketone and water or in a mixture thereof with use of an inorganic base.

2. Process according to claim 1, wherein the solvent is a ketone or a mixture of ketone and water.

3. Process according to claim 1, wherein the inorganic base is sodium hydroxide, sodium carbonate or sodium bicarbonate.

4. Process according to claim 1, wherein the solvent is an acetone/water mixture and the base is sodium carbonate.

5. Process according to claim 1, comprising initially charging an aqueous sodium carbonate solution, adding the reactants at a temperature between 10 and 15° C., and then stirring the reaction mixture at 50° C.

6. Process according to claim 1, comprising recrystallizing the obtained crude product 5-chloro-N-({(5S)-2-oxo-3-[4-(3-oxo-4-morpholinyl)phenyl]-1,3-oxazolidin-5-yl}methyl)-2-thiophenecarboxamide from acetic acid in a subsequent step.

7. Process according to claim 1, comprising preparing 4-{4-[(5S)-5-(aminomethyl)-2-oxo-1,3-oxazolidin-3-yl]phenyl}morpholine-3-one hydrochloride by eliminating the phthalimide protective group from 2-({(5S)-2-oxo-3-[4-(3-oxo-4-morpholinyl)phenyl]-1,3-oxazolidin-5-yl}methyl)-1H-isoindole-1,3(2H)dione with methylamine in ethanol as solvent, and isolating 4-{4-[(5S)-5-(aminomethyl)-2-oxo-1,3-oxazolidin-3-yl]phenyl}morpholine-3-one as solid hydrochloride.

8. Process according to claim 7, comprising adding aqueous hydrochloric acid to the reaction mixture at a temperature between 50 and 60° C. until the pH is between 2 and 3 after reacting 2-({(5S)-2-oxo-3-[4-(3-oxo-4-morpholinyl)phenyl]-1,3-oxazolidin-5-yl}methyl)-1H-isoindole-1,3(2H)dione with methylamine.

9. Process according to either of claims 7 or 8, comprising preparing 2-({(5S)-2-oxo-3-[4-(3-oxo-4-morpholinyl)phenyl]-1,3-oxazolidin-5-yl}methyl)-1H-isoindole-1,3(2H)dione by cyclization of 2-((2R)-2-hydroxy-3-{[4-(3-oxo-4-morpholinyl)-phenyl]amino}propyl)-1H-isoindole-1,3(2H)dione with a phosgene equivalent, wherein the reaction is carried out in toluene as solvent.

10. Process according to claim 9, comprising isolating 2-({(5S)-2-oxo-3-[4-(3-oxo-4-morpholinyl)phenyl]-1,3-oxazolidin-5-yl}methyl)-1H-isoindole-1,3(2H)dione by filtration.

11. Process according to claim 9, comprising preparing 2-((2R)-2-hydroxy-3-{[4-(3-oxo-4-morpholinyl)phenyl]amino}propyl)-1H-isoindole-1,3(2H)dione by reacting 2-[(2S)-2-oxiranylmethyl]-1H-isoindole-1,3(2H)-dione with 4-(4-aminophenyl)-3-morpholinone in aqueous ethanol as solvent, wherein the ethanol/water ratio is 1:2.

12. Process according to claim 11, comprising adding seed crystals of the reaction product 2-((2R)-2-hydroxy-3-{[4-(3-oxo-4-morpholinyl)phenyl]amino}propyl)-1H-isoindole-1,3(2H)dione to the reaction mixture after the reaction has lasted from one to two hours.

13. Process according to claim 12, comprising heating the reaction mixture under reflux twice towards the end of the reaction time and on each occasion subsequently cooling said reaction mixture again to a reaction temperature of between 55 and 65° C.

14. The process of claim 9, wherein the phosgene equivalent is N,N-carbonyldiimidazole.

* * * * *